(12) United States Patent
Anile (10) Patent No.: US 9,168,363 B2
(45) Date of Patent: Oct. 27, 2015

(54) IMPLANTABLE DEVICE FOR THE TREATMENT OF HYDROCEPHALUS SYNDROME AND THE CORRESPONDING METHOD

(71) Applicant: SIAD HEALTHCARE S.P.A., Assago (IT)

(72) Inventor: Carmelo Anile, Assago (IT)

(73) Assignee: SIAD HEALTHCARE S.P.A., Assago (IT)

( * ) Notice: Subject to any disclaimer, the term of this patent is extended or adjusted under 35 U.S.C. 154(b) by 0 days.

(21) Appl. No.: 14/373,432

(22) PCT Filed: Jan. 23, 2013

(86) PCT No.: PCT/EP2013/051197
§ 371 (c)(1),
(2) Date: Jul. 21, 2014

(87) PCT Pub. No.: WO2013/110634
PCT Pub. Date: Aug. 1, 2013

(65) Prior Publication Data
US 2015/0005800 A1    Jan. 1, 2015

(30) Foreign Application Priority Data
Jan. 27, 2012   (IT) .............................. MI2012A0097

(51) Int. Cl.
*A61B 5/03*      (2006.01)
*A61M 29/02*     (2006.01)
*A61M 27/00*     (2006.01)

(52) U.S. Cl.
CPC ............. *A61M 29/02* (2013.01); *A61M 27/006* (2013.01); *A61B 5/031* (2013.01)

(58) Field of Classification Search
CPC ..... A61M 27/006; A61M 29/02; A61B 5/031
See application file for complete search history.

(56) References Cited

U.S. PATENT DOCUMENTS 3,958,558 A * 5/1976 Dunphy et al. ............... 600/407
4,014,319 A * 3/1977 Favre ............................ 600/561
(Continued)

FOREIGN PATENT DOCUMENTS

WO       WO0205710 A2    1/2002

OTHER PUBLICATIONS

Search and Written Opinion for PCT/EP2013/051197 issued on Mar. 12, 2013.

*Primary Examiner* — Sean Dougherty
(74) *Attorney, Agent, or Firm* — Silvia Salvadori, P.C.

(57) ABSTRACT

Implantable device or the treatment of hydrocephalus in a patient, comprising movement means designed to move the cerebrospinal fluid in the patient's skull to control the intracranial pressure; an assembly consisting of a rotary volumetric micropump; a catheter connected at one extremity to the micropump; and a bag fitted at the other extremity of the catheter and designed to contract and expand, wherein said assembly is filled with a given volume of a service fluid which remains constant over time, and wherein electronic monitoring and control means are designed to process the values (Pmis), as detected by a sensor of the instant pressure of cerebrospinal fluid and to generate a corresponding control signal which in turn drives the micropump and consequently controls the contraction and expansion of the bag so that the amplitude of the variable component of the intracranial pressure due to the cardiac cycle is minimized.

12 Claims, 4 Drawing Sheets

(56) References Cited

U.S. PATENT DOCUMENTS

| | | | |
|---|---|---|---|
| 4,281,666 A | 8/1981 | Cosman | |
| 4,281,667 A * | 8/1981 | Cosman | 600/561 |
| 4,601,724 A * | 7/1986 | Hooven et al. | 604/264 |
| 4,627,443 A | 12/1986 | Chubbuck et al. | |
| 4,723,556 A | 2/1988 | Sussman | |
| 7,510,533 B2 * | 3/2009 | Mauge et al. | 600/561 |
| 8,292,856 B2 * | 10/2012 | Bertrand et al. | 604/317 |
| 2005/0228315 A1 * | 10/2005 | Ayad | 600/587 |
| 2008/0139959 A1 * | 6/2008 | Miethke et al. | 600/561 |
| 2009/0204019 A1 * | 8/2009 | Ginggen et al. | 600/561 |
| 2009/0287084 A1 * | 11/2009 | Ragauskas et al. | 600/454 |
| 2011/0066072 A1 * | 3/2011 | Kawoos et al. | 600/561 |
| 2012/0221082 A1 * | 8/2012 | Khanna | 607/105 |

\* cited by examiner

IMPLANTABLE DEVICE FOR THE TREATMENT OF HYDROCEPHALUS SYNDROME AND THE CORRESPONDING METHOD

This application is a U.S. national stage of PCT/EP2013/051197 filed on 23 Jan. 2013 which claims priority to and the benefit of Italian Application No. MI2012A000097 filed on 27 Jan. 2012, the contents of which are incorporated herein by reference in their entireties.

FIELD OF INVENTION

The present invention relates in general to the treatment of hydrocephalus syndrome or hydrocephalus, and in particular to a device implantable in a patient to implement said treatment.

The invention also relates to a corresponding method for the treatment of hydrocephalus syndrome.

BACKGROUND TO THE INVENTION AND STATE OF THE ART

Hydrocephalus syndrome still represents a complex, difficult challenge, as regards not only understanding of the pathogenetic mechanisms underlying it, but also the identification and implementation of the best possible treatment method.

Numerous pathogenetic hypotheses of hydrocephalus have been proposed in the last few decades.

For the sake of completeness, the hypotheses which have been and are currently most widely accredited will be described briefly below.

The Cerebrospinal Fluid "Circulation" Hypothesis

The first hypothesis, which is also the most widely accepted, is based on the assumption that cerebrospinal fluid (CSF) "circulates" from the choroidal plexuses of the cerebral ventricles, its final destination being the arachnoid granulations of the cerebral convexity.

According to this theory, an obstacle to this "circulation" at any level and by any means, caused, for example, by stenosis of the aqueduct, a tumour of the posterior cranial fossa, or reduced absorption following haemorrhagic or infectious events affecting the subarachnoid spaces, gives rise to "obstructive" or "non-communicating" hydrocephalus as well as "non-obstructive" or "communicating" hydrocephalus.

Leaving aside the theoretical arguments and the extensive set of indirect, clinical and experimental data contradicting the pathogenetic hypothesis of an obstacle to the outflow of CSF, what finally demolished this first hypothesis was "direct" evidence, in human and animal models, of the absence of "circulation" of cerebrospinal fluid, at least in the form it would need to take in order for a mechanism involving an "obstacle" to that circulation to produce significant ventricular dilation.

In other words, it has been extensively demonstrated firstly that there is a "diffusion", not a movement of volume (ie. "circulation") of CSF in the intracranial system, so that the sites where CSF is produced are also responsible for its absorption and vice versa, and secondly that the movement of CSF inside and outside the ventricular cavities is constituted by a periodic oscillation synchronous with the cardiac pulsation, but without a real "net flow" in either direction.

This last finding is based on extensive medical literature on the subject, bearing in mind that the fundamental variable to be considered is always the rate of flow, namely the "void signal".

In fact, the data obtained by experimental measurement must be suitably corrected to take account of the variation in the gauge of the structure in which the measurement is taken (usually the mesencephalic duct), which periodically narrows during systole, thus causing an increase in the speed (but not the flow), and widens during diastole, causing the opposite effect which exactly offsets the previous one, thus confirming the absence of a "net flow", and consequently of true "circulation" of CSF.

The "Ventricular Pulse Pressure" Hypothesis

The second hypothesis is based on the observation that hydrocephalus, whether clinical or experimental, is very often associated with an increase in the "CSF pulse pressure", namely the difference between the maximum and minimum values of the intracranial pressure during each cardiac cycle.

If this second hypothesis is analysed on the basis of an intracranial system model with a rigidly constant volume, a different explanation can be formulated for the onset of hydrocephalus syndrome, namely that the development of hydrocephalus of any type, regardless of its etiology, is produced by the association between the "intraventricular pulse pressure of the choroid plexuses" and an "asymmetrical response" by the cerebral parenchyma.

In particular, this second hypothesis takes account of a behavioural characteristic well known in the literature in relation to viscoelastic substances, with which the cerebral parenchyma has always been compared in anatomical and structural terms.

This means that the brain, as a result of the pulsating force acting on it, is more easily "compressible" (during systole) then "expandable" (during diastole) at the end of the compression phase.

The continual alternation between systole (compression) and diastole (expansion) leads to a progressive reduction in cerebral volume and consequently an increase in ventricular volume, until a new balance is reached between the forces acting in the two directions that will determine the actual dimensions of the cerebral ventricles, from normal or relatively normal volumes to the extreme degrees of hydrocephalus syndrome.

The factors illustrated above explain why the current systems used to treat hydrocephalus, mainly based on the use of "CSF shunts" which move part of the CSF volume from the intracranial system to other body cavities, can provide no more than a partial, indirect, imprecise solution to the pathogenetic alteration postulated here.

This incongruity clearly explains the limitations still involved in the conventional treatment of hydrocephalus syndrome.

A radical solution to the problem only seems to be possible if one or both of the two factors illustrated above can be modified, namely the "intraventricular pulse pressure" and the "asymmetrical response" of the cerebral parenchyma.

REFERENCE TO A PRIOR PATENT APPLICATION DESIGNATING THE SAME INVENTOR

In the same field as the present invention, namely the treatment of hydrocephalus syndrome and devices usable in said treatment, there is a prior Italian patent application, no. RM2006A00592, filed on 2 Nov. 2006 and granted as no. 0001372554, entitled "Implantable device for treatment of the hydrocephalus syndrome" designating the same inventor as the present patent application.

Said prior patent application, starting from the context illustrated above and the various hypotheses, especially the second, which were formulated to justify the treatment used for hydrocephalus syndrome, relates to a rotary volumetric micropump which, when suitably driven, drains CSF from the skull and moves it to an accumulator when the intracranial pressure (ICP) value needs to be reduced, and returns it to the skull when the ICP needs to be increased.

However, the pump disclosed in said prior patent application appears to suffer from some limitations and drawbacks, and therefore needs to be perfected.

In particular, some important mechanical parts of the micropump, such as the rotary element, are not isolated from the cerebrospinal fluid (CSF), but come into direct contact with it, with the consequent risk that in the event of breakage of or damage to said rotary element, fragments thereof may be released into the cerebrospinal fluid.

There are also problems of biocompatibility between said mechanical parts and the cerebrospinal fluid which cannot be ignored, but require a practical, effective solution.

In fact, the presence of a certain proportion of protein material, which is normally already dissolved in the cerebrospinal fluid, may prejudice the operation of the micropump with time if the moving mechanical parts come into contact with said material, which would obstruct its movement when it coagulates.

PURPOSE AND SUMMARY OF THE INVENTION

The primary purpose of the present invention is therefore to make significant, tangible improvements to the treatment of hydrocephalus syndrome, and in particular, for that purpose, to provide a device implantable in a patient in the course of said treatment which, starting from the description contained in Italian patent application RM2006A00592 of 2 Nov. 2006, substantially improves its performance and safety.

Said purposes can be deemed to be fully achieved by the device implantable in a patient for the treatment of hydrocephalus syndrome having the characteristics defined by independent claim 1.

Particular forms of embodiment of the present invention are defined by the dependent claims.

Advantages of the Invention

Specifically, the starting point of the device according to the present invention is a method of treating hydrocephalus syndrome which is designed to modify the CSF pulsation generated in the skull by the cardiac pulsation, and for that purpose includes a system that actively monitors the CSF pulsations according to the actual needs required by the hydrocephalus syndrome at all times in the patient's everyday life.

The device thus meets the need for adequate, effective treatment of hydrocephalus syndrome and the need to avoid haemorrhagic complications, which are still relatively frequent with the current treatment systems involving "hyperdrainage" of CSF from the skull.

Said haemorrhagic complication is largely due to the methodology used in the current systems.

In fact, said known systems only act as differential valves between the intracranial pressure (ICP) and the pressure in the extracranial, peritoneal or right cardiac atrium site of collection of cerebrospinal fluid (CSF), without monitoring the absolute value of the ICP, thus generating said drawback.

Conversely, as the device according to the present invention only acts in response to instant detection of the intracranial pressure (ICP) and does not involve any drainage of cerebrospinal fluid (CSF), as described in detail below, it wholly eliminates the risk that such a complication may arise.

Moreover, the device according to the present invention substantially improves the implantable device disclosed by said Italian patent application 2006RM00592, and in particular achieves the same results, without the same drawbacks, as the rotary volumetric micropump included in the device to which said prior application relates, by using a bag with highly yielding walls designed to be filled and emptied by injection or removal of a suitable service fluid.

In this way, the following substantial benefits are obtained compared with the device disclosed in Italian patent RM2006A00592:

the rotating mechanical part of the pump is completely isolated and separated from the cerebrospinal fluid, so that if said rotating part is damaged, any fragments thereof remain in the device and are not released into the cerebrospinal fluid;

although the service fluid used to fill and empty the bag must possess characteristics of biocompatibility, it can be selected with a wide degree of freedom so as to maximise the durability of the device; for example, liquid wholly devoid of material liable to damage the pump mechanisms, possibly with lubricating properties, can be used.

BRIEF DESCRIPTION OF DRAWINGS

These and other purposes, characteristics, methods of use and advantages of the present invention will clearly emerge from the following description of a preferred embodiment thereof, given by way of example but not of limitation, with reference to the annexed drawings, wherein.

DESCRIPTION OF A PREFERRED EMBODIMENT OF THE IMPLANTABLE DEVICE ACCORDING TO THE INVENTION FOR THE TREATMENT OF HYDROCEPHALUS SYNDROME

Figure 1:
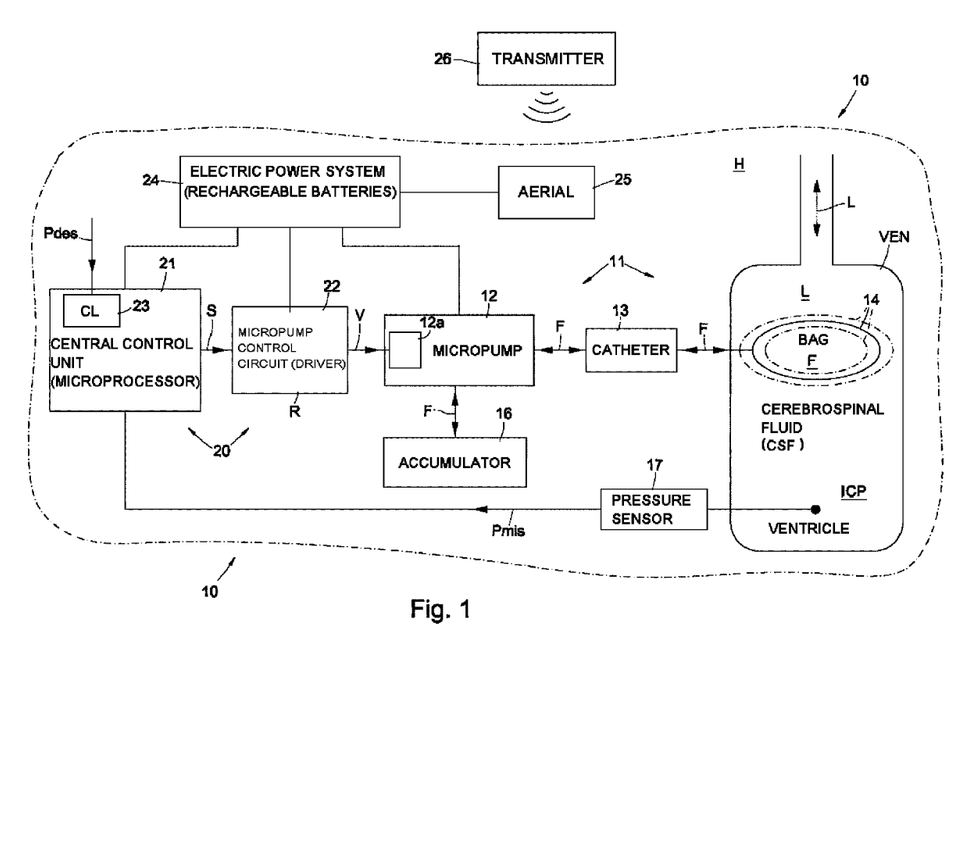
FIG. 1 is a functional block diagram of a device according to the present invention which can be implanted in a patient's head for the treatment of hydrocephalus syndrome.

With reference to the drawings, a device according to the present invention, suitable to be implanted in the head of a patient for the treatment of hydrocephalus syndrome, is indicated as a whole as 10 and schematically represented in FIG. 1 in the form of functional blocks.

As will be clear from the rest of the description, the salient feature of device 10 according to the invention is that it measures the intracranial pressure ICP which acts in cerebrospinal fluid CSF during each cardiac cycle of the patient, and determines, on the basis of a specific algorithm and taking account of the measured pressure, the variation in volume of a bag, fitted to implantable device 10 and inserted into a cerebral ventricle of the patient, in order to adapt the CSF pulsation to the requirements of the hydrocephalus syndrome treatment.

In particular, device 10 is designed to control the variation in volume of said bag so as to drain a certain amount of cerebrospinal fluid CSF from the cerebral ventricle during the systolic phase, and to return a similar quantity of cerebrospinal fluid CSF to the same cerebral ventricle during the diastolic phase of the cardiac cycle.

This method of operation of device 10 according to the invention, using a bag of variable volume to move cerebrospinal fluid CSF from and to the cerebral ventricle, represents a substantial improvement on the direct movement of cerebrospinal fluid CSF from and to the cerebral ventricle proposed in prior patent application RM2006A00592, which designates the same inventor as the present patent application.

In detail, implantable device 10 comprises:

movement means, implantable in the patient, indicated as a whole as 11, designed to move cerebrospinal fluid CSF in the patient's skull in order to control the intracranial pressure ICP of cerebrospinal fluid CSF contained in the patient's skull;

measuring means, typically consisting of a pressure sensor 17, having the function of measuring the instant intracranial pressure ICP present in cerebrospinal fluid CSF in the skull, and therefore providing the data and values, indicated as Pmis, of said intracranial pressure ICP; and electronic monitoring and control means, indicated in general as 20, designed to process the Pmis data indicating intracranial pressure ICP, detected by the measuring means, ie. by sensor 17, and to govern the operation of device 10 on the basis of said Pmis data.

Movement means 11 in turn are constituted by an assembly consisting of:

a micropump 12;

an intraventricular catheter 13, also called a catheter, connected at one extremity to micropump 12;

a balloon-shaped bag 14, made of yielding material, associated with the other extremity of catheter 13, distal to micropump 12, wherein said bag 14 is designed to be inserted into a cerebral ventricle VEN of the patient; and an accumulation tank or expansion chamber 16, also called the tank or accumulator, hydraulically connected to micropump 12.

Bag 13, micropump 12 and tank 14 are filled with a given volume of a biocompatible liquid, which remains constant over time, hereinafter called the "service fluid" of "fluid" and indicated as F, which possesses chemical-physical characteristics that guarantee reliable operation of micropump 12 over time.

For example, said service fluid F may consist of a protein-free liquid which has lubricating properties.

In operation, as described in more detail below, fluid F is designed to be moved, by suitably activating micropump 12, from bag 14 to accumulator 16 or vice versa, so as to contract or expand the volume of bag 14 in order to modify or even cancel, depending on the desired pattern, the pulsating or waveform component of intracranial pressure ICP.

Micropump 12 has no valves and is the rotary volumetric type; in other words, it comprises a rotating element designed to move a volume of fluid F from a suction or inlet area to a delivery or outlet area of said micropump 12, so that the volume of fluid F moved is determined by the number of revolutions performed by the rotary element of micropump 12.

Micropump 12 in turn is driven by an electric motor 12a, preferably of the brushless, reluctance or step type wherein, during operation, said motor 12a can be controlled in the "four quadrants" (two-way) mode.

Advantageously, motor 12a can also be used as a generator to partly recharge a system of batteries, more particularly described below, that power device 10.

Motor 12a is also fitted with a sensor, for example constituted by an encoder, designed to measure the number of revolutions, so that the flow rate of micropump 12 can also be measured indirectly.

Motor 12a, which controls the rotation of volumetric micropump 12, is designed to be controlled by a control or driver circuit included in electronic monitoring and control means 20 and indicated as 22 in the block diagram in FIG. 1.

In particular, said control circuit 22 is designed to control in both directions, and at a controlled angular speed, the rotation of motor 12a and consequently also the pumping of fluid F in one direction or the other through micropump 12, in order to keep the intracranial pressure ICP acting in the skull constantly under control.

In this way, as will clearly appear from the rest of the description, control circuit 22, designed to monitor and vary the number of revolutions and the direction of rotation of motor 12a, or of the rotating part of volumetric micropump 12, corresponds to and operates as a pressure regulator R designed to regulate the value of intracranial pressure ICP and keep it under control over time.

The angular rate of rotation, and consequently the number of revolutions of motor 12a which controls the rotating element of micropump 12, in turn depends on a control voltage V, with which control circuit 22 or pressure regulator R powers and controls said motor 12a, according to the construction characteristics of the latter and, as already stated, in order to monitor intracranial pressure ICP.

In detail, control circuit 22 which controls motor 12a, and consequently micropump 12, with voltage V, can be, for example, the proportional type with a lead compensator, or with a zero and a pole, wherein the ability of control circuit 22 to operate proportionally determines the precision of the monitoring system, and the lead compensator filters the error signal of the intracranial pressure in relation to the pole and defines the characteristics and performance of the monitoring system during transitory periods.

The parameters of control circuit 22 or pressure regulator R can be defined by classic linear controller design techniques once the characteristics of micropump 12 and motor 12a to be used in device 10 have been identified and established.

In the operation of device 10, as described in more detail below, control voltage V, with which control circuit 22 controls motor 12a to determine the number of revolutions, the direction of rotation, the flow rate of micropump 12, and consequently the volume of fluid F moved from micropump 12 in one direction or the other, is determined and tied to the pattern over time of the actual intracranial pressure ICP by a formula or control law CL of the type:

$$V(z)=R(z)(\text{Pdes}(z)-\text{Pmis}(z)) \quad \text{(CL)}$$

wherein:
R(z) is the transform z of pressure regulator R, ie. of control circuit 22 that controls micropump 12;
Pmis is the measured actual value of intracranial pressure ICP, as measured by pressure sensor 17; and
Pdes is the desired pre-set value of intracranial pressure ICP to be maintained over time by implantable device 10.

The sampling interval at which, during operation, control unit 21 of device 10 samples and measures intracranial pressure ICP via sensor 17, in order to calculate, on the basis of said formula, the value of voltage V to be applied to motor 12a via control circuit 22, is preferably approx. 5 ms (200 Hz).

Moreover, the regulation of micropump 12 by control circuit 22 or regulator R is subject to the constraint that the total flow rate of cerebrospinal fluid CSF in a given period of time must be nil.

Figure 2:
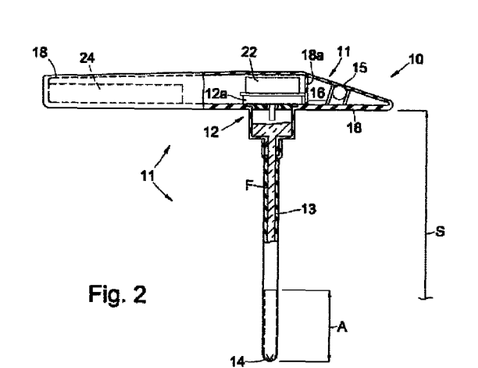
FIG. 2 is a partial lateral schematic view, with some parts in cross-section, of the implantable device according to the invention shown in FIG. 1, including a micropump, a catheter and a contractable and expandable bag, the bag being shown in its folded configuration before the device according to the invention is implanted into the patient.

Intraventricular catheter 13, which is connected to micropump 12 at one extremity and fitted with bag 14 at a second distal extremity, presents a cross-sectional area a and a length similar to that of the catheters used to make the conventional shunts, so that catheter 13 is suitable to be treated with the same procedures and using the equipment currently available in operating theatres.

Bag 14, made of yielding material, consists, for example, of waterproof fabric, and has a maximum pre-set volume of, for example, 2 cm3.

Figures 3, 4, 5:
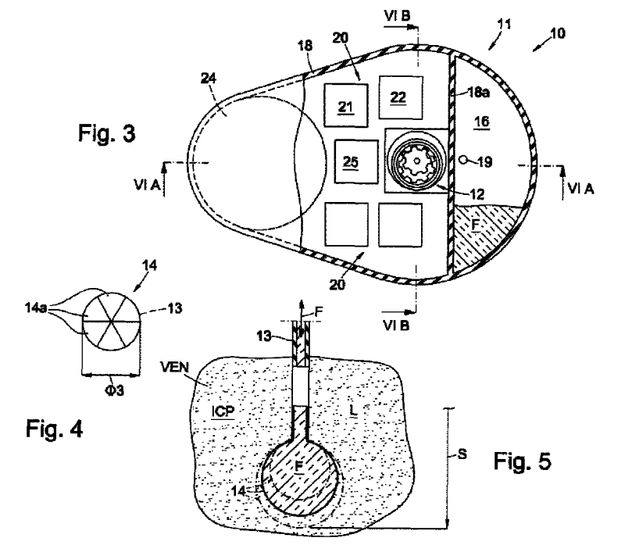
FIG. 3 is a partial schematic plan view of the implantable device illustrated in FIG. 2.
FIG. 4 is a schematic view, on an enlarged scale, of the bag illustrated in FIG. 2, in its folded configuration before the device according to the invention is implanted into the patient.
FIG. 5 is a schematic view, in cross-section, of the bag shown in FIGS. 2 and 4, in the working configuration adopted during full-scale operation of the device according to the invention, once implanted into the patient's head.

As shown in FIG. 4, bag 14, before and during positioning of device 10 in the patient's head, presents a folded configuration wherein bag 14 is contained and kept folded in the distal extremity of catheter 13, ie. the extremity not connected to micropump 12, so as to present a closed configuration in the form of "petals", which are shown as 14a, and overall dimensions not exceeding the diameter of the ventricular catheters normally used, for example 2.7 mm.

Bag 14 also presents some markers designed to measure its dimensions during the stage of installation and positioning in the patient's head.

Sensor 17 for measurement of instant intracranial pressure ICP is preferably integrated into the same extremity of catheter 13 that is connected to bag 14, and is consequently designed to be inserted into the patient's ventricle.

In detail, pressure sensor 17 is the commercial type and its performance, dimensions and biological compatibility characteristics are equal or similar to those of the sensors currently used at the diagnostic stage during infusion tests.

Said currently available pressure sensors, in particular such as the one made by CODMAN, present a "drift" over time, e.g. of 3 mmHg/24 h, in an operational range of ±50 mmHg max.

However, said drift does not affect the performance of device 10 according to the present invention, as it requires, for the treatment of hydrocephalus, control of the variable component of the intracranial pressure, not the average pressure, as described in greater detail below.

Accumulator 16, which communicates with micropump 12, consists of a chamber with a variable volume, the expansion/contraction of which is obtained via a bellows element containing a biologically compatible inert gas, or a suitable variable volume consisting of expanded cellular plastic, housed in said accumulator 16.

Alternatively, accumulator 16 can be fitted with a yielding wall.

Electronic monitoring and control means 20 comprise a central control unit 21, for example consisting of a microprocessor, microcontroller, an FPGA (Field Programmable Gate Array) component, or any other programmable digital device, wherein said central control unit 21 is designed to control, via a control signal S, control circuit 22 already described, which in turn is designed to control, at voltage V, motor 12a which activates micropump 12.

Central control unit 21 implements and incorporates suitable programs and algorithms 23, such as the control law CL illustrated above, on the basis of which it analyses the instant pattern of intracranial pressure ICP, as described in greater detail below, and consequently monitors control circuit 22 which controls micropump 12.

To sum up, central control unit 21 is programmed to perform the following functions:
analog/digital conversion for reading the measurement signal of the Pmis pressure generated by sensor 17;
count of number of revolutions of micropump 12;
storage of desired value or pattern Pdes of intracranial pressure ICP;
calculation of control signal, or of voltage V, for motor 12a of micropump 12, in order to reduce and eliminate any difference between the actual measured intracranial pressure Pmis and the desired pressure Pdes;
supervisory functions, in particular relating to control of the net flow drained during a period;
determination of the conditions under which it is necessary or unnecessary to modify the pressure waveform;
storage of error conditions;
management of inward and outward transmission of information via the aerial;
management of recharging of power pack batteries.

Control circuit 22 for driving micropump 12 can consist of a power amplifier which provides, in reply to signal S generated by central control unit 21, the power, corresponding to voltage V, required for operation of said micropump 12.

The entire implantable device 10 is powered by an electrical system or circuit, indicated as 24 and consisting of rechargeable batteries, wherein the energy for recharging the batteries is transmitted electromagnetically from the exterior via a transmitter 26 that communicates with an aerial 25 associated with power system 24.

Said aerial 25, as well as receiving the energy required for the operation of device 10, can advantageously be used to transmit data and information from device 10 to the exterior and to receive the commands and parameters sent by transmitter 26 which are needed to calibrate device 10.

Figures 6A, 6B, 6C, 7A, 7B:
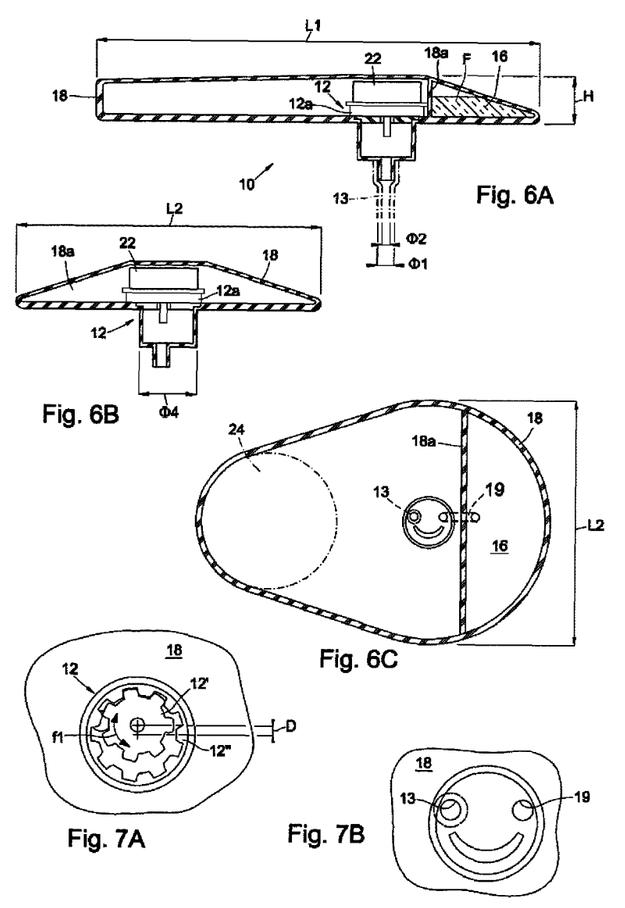
FIGS. 6A, 6B are further partial schematic views, in cross-section, along lines VI A-VI A and VI B-VI B shown in FIG. 3, of the implantable device according to the invention.
FIG. 6C is a cross-section which shows a plan view of the base of an outer shell of the implantable device illustrated in FIG. 2.
FIGS. 7A and 7B are views on an enlarged scale of some areas and details of the micropump shown in FIG. 2.

A flat outer shell 18, shown in plan view in FIGS. 3 and 6C, houses micropump 12, the electronic components schematically illustrated in block form in FIG. 3, which constitute the monitoring and control means 20 of implantable device 10, and rechargeable battery system 24.

FIGS. 6A-6C also show said shell 18 laterally, frontally and from above in cross-section with some of the parts of device 10, such as micropump 12, housed in shell 18.

A portion of the extremity of outer shell 18 also forms storage tank 16, which is separated by a wall 18a from the remaining internal volume of shell 18 and communicates with micropump 12 via a tube 19.

A filling valve 15, installed along the surface of outer shell 18 and schematically illustrated in FIG. 2, is fitted to allow the system consisting of accumulator 16, micropump 12 and catheter 13 to be filled with fluid F.

FIGS. 7A-7B schematically illustrate some areas and details of volumetric micropump 12, and in particular an inner cogwheel, indicated as 12', housed in and meshing with an outer cogwheel, indicated as 12", of said micropump 12.

The two cogwheels 12' and 12" are therefore offset from one another by a distance D, as shown in FIG. 7A.

In operation, inner cogwheel 12', rotating in one direction or the other as indicated by double arrow f1 in FIG. 7A, causes the rotation of outer cogwheel 12" and consequently determines, proportionally to the number of revolutions effected, the volume of fluid F moved from tank 16 to catheter 13, and therefore to bag 14, or conversely from catheter 13, and therefore from bag 14, to tank 16.

Finally, for the sake of completeness and purely by way of example, some dimensional and operational data and information relating to implantable device 10 according to the present invention, and its component parts, are given below by reference to the drawings.

As will be seen from said data, in terms of construction, device 10 has a shape and dimensions such that it can easily be implanted into the head of a patient, in the subcutaneous space on the skull.

Salient External Dimensions of Device
L1=65.4 mm
L2=45 mm
H=7 mm
S=60 mm
A=12 mm
Φ4=8.5 mm
Volumetric Micropump
Maximum flow rate of micropump: q=2 cm3/s
Nominal pressure: pnom=40 mmHg=5263 Pa
Maximum pressure: pmax=100 mmHg
Transmission ratio between inner cogwheel and outer cogwheel=7/9
Catheter and Bag
Φ1=2.7 mm
Φ2=1.4 mm
Φ3=2.7 mm
Powers and Absorption
Average nominal power Wnom=pnom×q=5263×2e-6=0.0105 W
Average power, with motor efficiency of 0.50 and pump efficiency of 0.50=0.042 W
Power absorbed by electronics estimated at 0.042 W.
The total power is therefore 0.084 W, rounded up to 0.10 W.
Assuming that the device operates for at least 4 hours a day when fully operational, an 0.40 Wh, 3.3 V (120 mAh) battery is required.

The battery is recharged electromagnetically during the 8 hours of sleep; for the purpose of said recharge, it is therefore necessary to transmit power amounting to 0.40 Wh/8 hours=0.050 W, which can easily be effected by transcutaneous commercial radio transmitters.

Operation of Device According to the Invention

The application procedures and operation of implantable device 10 according to the invention for the treatment of hydrocephalus syndrome will now be described by reference to the block diagram in FIG. 8.

At a preliminary stage indicated as 31 which precedes its use and operation, device 10 is obviously implanted and positioned by the surgeon in the patient's head.

In more detail, under simple local anaesthetic, the surgeon makes a curved incision with convexity towards the median line on the frontal region, preferably on the right to avoid penetrating the dominant hemisphere, in the area immediately in front of the coronal suture.

The surgeon then exposes the frontal bone, drills a hole of the usual dimensions, for example 9 mm in diameter, makes an incision in the dura mater after coagulation, and then performs a frontal ventriculostomy with a Cushing probe.

When the exit of cerebrospinal fluid CSF obtained with the Cushing probe has been verified, the surgeon introduces ventricular catheter 13, already connected to the part of device 10 containing micropump 12, through cerebral parenchyma CP into cerebral ventricle VEN, and at the same time positions accumulator 16 in a pre-formed subcutaneous bag in the incision.

After this positioning, the control software of device 10 pumps service fluid F contained in accumulator 16 via micropump 12, causing the exit of bag 14 from the tip area of catheter 13 in which it was folded, and its gradual filling with service fluid F originating from accumulator 16.

Figure 9:
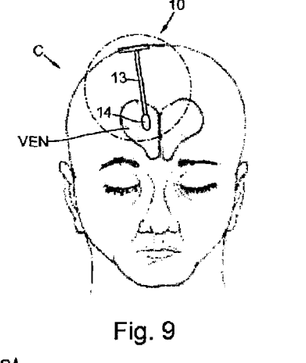
FIG. 9 is a view of a patient into whom a device according to the present invention for the treatment of hydrocephalus syndrome has been implanted.
Figure 9A:
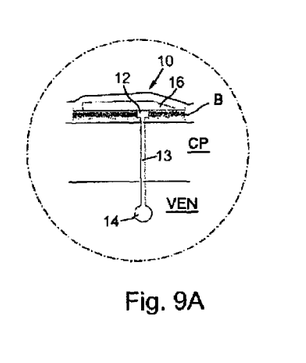
FIG. 9A is an enlarged view of the area in FIG. 9 indicated by a dotted and dashed circle.

For the sake of clarity, FIGS. 9 and 9A illustrate a scheme of positioning of device 10 in head H of a patient shown in front view.

As will be seen from FIGS. 9 and 9A, which show the contours of cerebral ventricles VEN in which catheter 13 connected to bag 16 containing service fluid F is positioned, micropump 12 is housed in bone B of the skull, and the remainder of device 10, comprising accumulator 16 and the control system of device 10, is positioned on it.

Once implanted in the patient, device 10 constantly measures the instant intracranial pressure value ICP during its operation via sensor 17, and sends the Pmis values thus measured to central control unit 21.

As the Pmis values measured by sensor 17 each correspond to the absolute current value of intracranial pressure ICP, said Pmis values are suitably processed and filtered by central control unit 21, so that insignificant pressure variations due, for example, to variations in the patient's posture, are not interpreted as errors compared with the desired pressure value Pdes which is to be kept under control.

Figure 8:
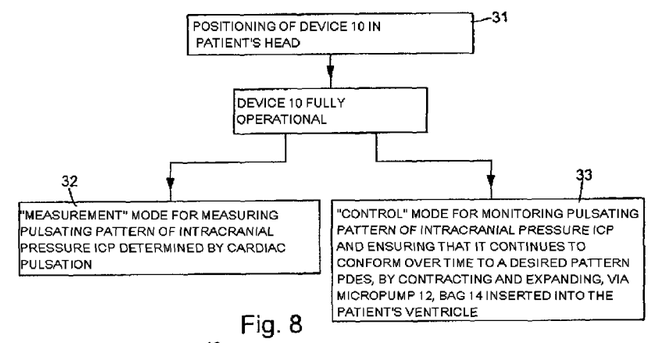
FIG. 8 is a block diagram that illustrates a method according to the present invention for the treatment of hydrocephalus syndrome.

When fully operational, device 10 operates in two modes: a first "Measurement" mode, indicated as 32 in FIG. 8, wherein micropump 12 is preferably inactive and stationary, and a second "Control" mode, indicated as 33 in FIG. 8, wherein micropump 12 is activated to move fluid F in a controlled way between bag 14 and accumulator 16.

"Measurement" Mode

In detail, in the first, "Measurement" mode, device 10 performs various measurements, via sensor 17, which correspond to a plurality of Pmis values of intracranial pressure ICP, without modifying it, only in order to measure its amplitude and waveform, as typically determined by the cardiac pulsation.

Central control unit 21 of device 10 also receives the measured Pmis values from sensor 17 and checks whether there is any difference between the pattern of the waveform, as measured, of intracranial pressure ICP and the pre-set desired pattern Pdes of said intracranial pressure ICP.

In normal full-scale operation of device 10, said "Measurement" mode is activated periodically to measure the intracranial pressure ICP of the cerebrospinal fluid CSF and at the same time to check the performance of said device 10.

Device 10 can also be activated to operate in said first "Measurement" mode when:
- the error between the measured pressure and the desired pressure exceeds a given value;
- micropump 12 is ordered to pump and move a high flow rate of fluid F; and
- rapid variations in intracranial pressure ICP take place, for example due to coughing, yawning or the like.

To sum up, in this "Measurement" mode, central control unit 21 of device 10 measures and acquires via sensor 17 the waveform of intracranial pressure ICP, as determined by the cardiac pulsation, wherein the values and data acquired include the peak-to-peak amplitude, the mean value of the wave of intracranial pressure ICP, and other parameters indicating its actual pattern.

Central control unit 21 also compares the data acquired with the pre-set desired pattern Pdes of intracranial pressure ICP, and checks whether the thresholds and variations compared with said desired pattern Pdes, which cause the activation of device 10 in the second "Control" mode, are complied with.

"Control" Mode

In the second, "Control" mode, device 10 operates actively, taking account of the pre-set desired form and pattern Pdes of the wave of intracranial pressure ICP to be monitored and maintained over time in the skull, wherein said pre-set desired form can also correspond to a constant value of Pdes or to a nil wave.

In particular, central control unit 21 activates micropump 12 via control circuit 22, according to the difference between desired intracranial pressure Pdes and the actual pressure acting in the skull, corresponding to the various Pmis values measured by sensor 17.

For example, this difference (Pdes−Pmis) can be calculated on the basis of the average of the desired Pdes values and/or the average of the actually measured Pmis values of intracranial pressure ICP.

Thus when intracranial pressure ICP, as measured by sensor 17, exceeds the desired pressure according to a given threshold, and intracranial pressure ICP consequently needs to be reduced to that it conforms to desired pattern Pdes, control unit 21 controls micropump 12 via control circuit 22, so as to remove a certain quantity of fluid F from bag 14 and introduce it into accumulator 16, or to remove fluid F from bag 14, which thus contracts, and transfer it to accumulator 16.

Conversely, when intracranial pressure ICP, as measured, is lower than the desired pressure according to a given threshold, and intracranial pressure ICP therefore needs to be increased so that it conforms to desired pattern Pdes again, control unit 21 controls micropump 12, via control circuit 22, so as to extract a certain quantity of fluid F from accumulator or tank 16 and introduce it into bag 14, or to remove fluid F from accumulator 16 and transfer it to bag 14, which thus expands.

Bag 14 therefore contracts or expands depending on whether it is filled with or emptied of fluid F, as schematically illustrated with a dotted and dashed line in FIG. 1.

In this "Control" mode, monitoring and control means 20 cooperate with dedicated program or software 23 to perform the calculations required to determine the operating parameters and correctly activate micropump 12.

In particular control unit 21 controls control circuit 22 via signal S so as to generate control voltage V for micropump 12, as defined by the following control law, already illustrated above:

$$V(z) = R(z)(\text{Pdes}(z) - \text{Pmis}(z))$$

Control unit 21 also determines and indirectly controls the flow rate, ie. the quantity of cerebrospinal fluid CSF moved from or to bag 14 to contract or expand it respectively, monitoring and counting the number of revolutions of volumetric micropump 12.

Tank 16 obviously has a sufficient capacity to accumulate, during the systolic cardiac phase, the quantity of fluid equal to the volume of cerebrospinal fluid CSF which must be drained from the skull to reduce the pulsating component of the intracranial pressure to the desired value.

It is also clear that in this continuous periodic transfer of fluid from bag 14 to tank 16 and vice versa, the average flow rate of fluid F through micropump 12 in a period is nil, as the volume of fluid F that fills bag 14 and tank 16, and is caused to circulate by micropump 12, is constant.

Moreover, as already stated, the use of the volumetric pump allows said flow to be measured indirectly by measuring the number of revolutions performed by said pump.

To sum up, for the sake of greater clarity, when the instant intracranial pressure exceeds the desired value, micropump 12 removes a quantity of fluid F from bag 14 and moves it to accumulator 16.

Conversely, when the instant intracranial pressure is lower than the desired value, micropump 12 removes a certain quantity of fluid F from accumulator or tank 16 and returns it to bag 14.

In this way, the increase and reduction in volume of bag 14 modify the instant value of intracranial pressure ICP so that it continues to conform over time to the desired value and pattern.

More specifically, control unit 21 controls the contraction and expansion of bag 14 in ventricle VEN, so that intracranial pressure ICP continues to conform over time to the pre-set desired pattern Pdes, and in particular so that the amplitude of the variable component of intracranial pressure ICP due to the cardiac cycle is minimised.

Figure 10:
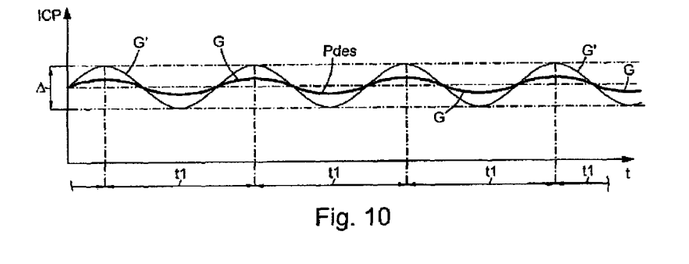
FIG. 10 is a graph that qualitatively shows the pattern over time of the "depulsated" intracranial pressure obtained with the device and method according to the invention.

To clarify, the graph in FIG. 10 shows and qualitatively compares the pattern G' over time t of intracranial pressure ICP which would occur in the absence of device 10 with pattern G obtained with device 10 according to the invention after being implanted into the patient's head.

As will be seen from said graph, although pattern G of intracranial pressure ICP exhibits a pulsating pattern determined by the cardiac pulsation of period t1 between the systolic and diastolic phases, it is considerably "depulsated", ie. presents a difference Δ between the maximum and minimum values considerably lower than pattern G', so as to reach desired pattern Pdes and continue to conform to it over time.

It is therefore clear that the present invention fully achieves its stated purposes, and in particular provides a device suitable to be implanted in a patient suffering from hydrocephalus syndrome in order to treat it, which said device operates reliably and safely over time.

Moreover, to ensure effective treatment of hydrocephalus syndrome, the implantable device according to the invention is able to "depulsate" the pulsating pattern of the intracranial pressure, as determined by the cardiac pulsation, to minimise pressure variations induced by said cardiac pulsation and therefore ensure that the intracranial pressure constantly conforms over time to a pre-set optimum pattern.

To sum up, the device achieves the purpose of optimally reducing or modifying the amplitude of the variable component of the intracranial pressure (ICP) due to the cardiac cycle, for the purpose of treating hydrocephalus syndrome.

Therefore, unlike conventional systems for the treatment of hydrocephalus, with the device according to the invention cerebrospinal fluid CSF is not continually drained from the skull and permanently transferred to another part of the patient's body.

Instead, cerebrospinal fluid CSF, without being permanently drained from the skull, is constantly monitored for pressure and the corresponding pulsating pattern, as determined by the cardiac pulsation, to ensure that said pressure constantly conforms over time to a desired pattern, and in particular that its oscillations are minimised, or even nil, so as to effectively "depulsate" intracranial pressure ICP acting in the skull.

Moreover, unlike known devices such as the one described in patent application RM2006A000592 already mentioned, the device according to the invention advantageously achieves complete separation between cerebrospinal fluid CSF and the rotating parts of the volumetric pump that controls its flow from and to the skull.

The present invention has so far been described by reference to a preferred embodiment thereof, but other forms of embodiment could be designed and conceived on the basis of the same invention concept, and therefore all fall within the scope of protection of the claims set out below.

The invention claimed is:

1. An implantable device for treatment of hydrocephalus syndrome in a patient, comprising:
    movement means, implantable in the patient, for moving and displacing cerebrospinal fluid (CSF) in the cranial site of the patient in order to control a value of an actual intracranial pressure (ICP) of said cerebrospinal fluid (CSF) in said cranial site;
    measuring means for measuring said actual intracranial pressure (ICP) and providing data (PMIS) indicative of its actual value, and
    electronic monitoring and control means for controlling operation of said device;
    said implantable device being characterized in that said movement means, implantable in the patient, comprise an assembly consisting of:
    a micropump;
    an intraventricular catheter connected at one end to said micropump;
    a bag, made of yielding material, associated with an other end of the catheter, said bag being designed to be inserted into a cerebral ventricle (VEN) of the patient; and
    an accumulation tank connected to said micropump;
    wherein said micropump, said catheter and said bag are filled with a certain volume of a service fluid (F) which remains constant over time, and
    wherein said micropump is designed to extract said service fluid (F) from said accumulation tank to supply said bag with said fluid, so as to dilate said bag in the ventricle, and to extract said service fluid (F) from said bag to supply said accumulation tank with said fluid, so as to contract said bag in the ventricle,
    whereby the dilation/contraction of said bag causes a corresponding variation of the intracranial pressure (ICP) of the cerebrospinal fluid (CSF) in the cranial site of the patient; and
    in that said electronic monitoring and control means is configured to process said data (Pmis) indicative of the intracranial pressure (ICP) and to generate a corresponding control signal (S, V), in turn configured to drive said micropump and thereby to control the contraction and dilation of said bag in the cerebral ventricle (VEN), in such a way that the pattern of the intracranial pressure (ICP) is maintained in time conforming to a pre-set desired pattern (Pdes).

2. Implantable device according to claim 1, comprising a flat outer shell which houses said micropump, wherein said accumulation tank is formed, inside said shell, by a portion of the latter and by a separation wall which separates said accumulation tank from the remaining interior space of said shell.

3. Implantable device according to claim 1, wherein said micropump is of a volumetric rotary type, and comprises an internal cogwheel and an external cogwheel, mutually meshed, whereby the volume of said service fluid (F) moved by said micropump is determined by the number of revolutions made by said micropump.

4. Implantable device according to claim 1, wherein said electronic monitoring and control means comprise a specific control circuit designed to generate a driving voltage (V) to drive said micropump, and
    wherein said electronic monitoring and control means are designed to process said data (Pmis) indicative of the intracranial pressure (ICP) in order to generate said driving voltage (V) for said micropump, on the basis of the following formula (CL):

$$V(z)=R(z)(\text{Pdes}(z)-\text{Pmis}(z))$$

where:
    R(z) is the transform of control circuit that drives micropump;
    Pmis is the effective and actual measured value of intracranial pressure (ICP), as measured by pressure sensor; and
    Pdes is the pre-set desired value of intracranial pressure (ICP) to be maintained over time, by means of implantable device.

5. Implantable device according to claim 1, wherein said bag exhibits, in the device not yet implanted in the patient, a folded configuration in which said bag is folded in the shape of petals inside the distal end of catheter not connected to said micropump.

6. Implantable device according to claim 1, wherein said service fluid (F), with which said micropump, said catheter and said bag are filled, exhibits chemical-physical characteristics suitable for ensuring reliable operation over time of micropump, said service fluid being constituted in particular by a protein-free liquid with lubricating properties.

7. A method for the treatment of hydrocephalus syndrome, comprising the following steps:
    implanting in the head of a patient a device for moving and displacing the cerebrospinal fluid (CSF) to and from the cranial site of the patient in order to control a value of an instant intracranial pressure (ICP) of said cerebrospinal fluid (CSF) in said cranial site, wherein said implantable device comprises at least one bag, made of yielding material, designed to be inserted into a cerebral ventricle (VEN) of the patient;
    continuously measuring, in a measurement mode by means of a pressure sensor of said device, the instant intracranial pressure (ICP) present in the cerebrospinal fluid (CSF) within the cranial site, so as to obtain values (Pmis) indicative of said intracranial pressure (ICP), and
    continuously controlling, in a control mode, the intracranial pressure (ICP) present in the cranial site, wherein said control stage comprises the steps of alternatively supplying said bag with a service fluid (F) and extracting said service fluid (F) from said bag, while taking continuously into account the values (Pmis) of said intracranial pressure (ICP) measured in said measurement mode, so as to control the contraction and dilation of said bag in the cerebral ventricle (VEN) in such a way that a pattern of the intracranial pressure (ICP) in the cranial site is maintained over time conforming to a pre-set desired pattern (Pdes).

8. Method for the treatment of hydrocephalus syndrome according to claim 7, wherein said bag is part of an assembly included in said device and consisting of:
a micropump;
an intraventricular catheter connected at one end to said micropump; and
an accumulation tank connected to said micropump;
said bag being associated with an other end of the catheter, which is insertable in the cerebral ventricle (VEN) of the patient,
wherein said micropump, said catheter and said bag are filled with a determined volume of said service fluid (F), which remains constant over time, and
wherein said micropump is designed to extract said service fluid (F) from said accumulation tank in order to supply said bag with said service fluid, so as to dilate said bag, and to extract said service fluid (F) from said bag to supply said accumulation tank with said service fluid, so as to contract said bag, in such a way that the pattern of the intracranial pressure (ICP) is maintained in time conforming to said pre-set desired pattern (Pdes).

9. A method for the treatment of hydrocephalus syndrome, comprising the following steps:
providing a device implantable into the head of a patient, comprising:
an assembly consisting of:
a micropump;
an intraventricular catheter connected at one end to said micropump;
a bag, made of yielding material, associated with an other, distal end of the catheter; and
an accumulation tank connected to said micropump;
a sensor designed to measure an instant intracranial pressure (ICP) present in the cerebrospinal fluid (C S F) within the cranial site; and
electronic monitoring and control means designed to govern operation of said device;
wherein said micropump, said catheter and said bag are filled with a given volume of a service fluid (F) which remains constant over time, and
wherein said micropump is designed to extract said service fluid (F) from said accumulation tank and introduce said service fluid into said bag, so as to dilate said bag, and to extract said service fluid (F) from said bag and introduce said service fluid into said tank, so as to contract said bag;
implanting said device by inserting the bag in a cerebral ventricle (VEN) of the patient;
continuously measuring with said sensor the instant intracranial pressure (ICP) present in the cerebrospinal fluid (CSF) inside the cranial site, so as to provide data (Pmis) indicative of said intracranial pressure (ICP), and
generating, with said electronic monitoring and control means and on the basis of said data (Pmis) indicative of the instant intracranial pressure (ICP), a corresponding control signal (S, V) designed to drive said micropump so as to control the contraction and dilation of said bag in the cerebral ventricle (VEN), in such a way that the pattern of the intracranial pressure (ICP) is maintained in time conforming to a pre-set desired pattern (Pdes).

10. The implantable device according to claim 1, wherein the amplitude of the variable component of the intracranial pressure (ICP) due to the cardiac cycle is minimised.

11. The method according to claim 7, wherein the amplitude of the variable component of the intracranial pressure (ICP) due to the cardiac cycle is minimised.

12. The method according to claim 9 wherein the amplitude of the variable component of the intracranial pressure (ICP) due to the cardiac cycle is minimised.

* * * * *